US009695341B2

(12) United States Patent
Thatcher et al.

(10) Patent No.: US 9,695,341 B2
(45) Date of Patent: Jul. 4, 2017

(54) ADHESIVES AND USE THEREOF

(71) Applicant: HENKEL IP & HOLDING GMBH, Duesseldorf (DE)

(72) Inventors: Jennifer Thatcher, Hamilton, NJ (US); Yuhong Hu, Belle Mead, NJ (US); Darshak Desai, Edison, NJ (US)

(73) Assignee: HENKEL IP & HOLDING GMBH, Duesseldorf (DE)

( * ) Notice: Subject to any disclaimer, the term of this patent is extended or adjusted under 35 U.S.C. 154(b) by 130 days.

(21) Appl. No.: 14/169,353

(22) Filed: Jan. 31, 2014

(65) Prior Publication Data

US 2014/0147669 A1    May 29, 2014

Related U.S. Application Data

(63) Continuation of application No. PCT/US2012/048131, filed on Jul. 25, 2012.

(60) Provisional application No. 61/515,013, filed on Aug. 4, 2011.

(51) Int. Cl.
| | |
|---|---|
| *C09J 123/20* | (2006.01) |
| *C08J 5/12* | (2006.01) |
| *C09J 123/10* | (2006.01) |
| *C09J 7/02* | (2006.01) |
| *C09J 5/00* | (2006.01) |
| *A61L 15/58* | (2006.01) |

(52) U.S. Cl.
CPC ............. *C09J 123/20* (2013.01); *C08J 5/125* (2013.01); *C09J 5/00* (2013.01); *C09J 7/021* (2013.01); *C09J 123/10* (2013.01); *A61L 15/58* (2013.01); *C08J 2423/12* (2013.01); *C08J 2423/20* (2013.01); *C08L 2314/02* (2013.01); *C08L 2314/06* (2013.01); *C09J 2201/61* (2013.01); *C09J 2423/00* (2013.01); *Y10T 428/2878* (2015.01)

(58) Field of Classification Search
CPC ...... C09J 123/10; C09J 123/12; C09J 123/14; C09J 123/142; C09J 123/18; C09J 123/20; C09J 123/22; C09D 123/10; C09D 123/12; C09D 123/14; C09D 123/142; C09D 123/18; C09D 123/20; C09D 123/22; C08L 23/10; C08L 23/12; C08L 23/14; C08L 23/142; C08L 23/18; C08L 23/20; C08L 23/22
See application file for complete search history.

(56) References Cited

U.S. PATENT DOCUMENTS

| 4,022,728 | A | * | 5/1977 | Trotter et al. ................ 524/528 |
|---|---|---|---|---|
| 4,178,272 | A | * | 12/1979 | Meyer, Jr. ............ C09J 123/142 524/271 |
| 4,233,432 | A | | 11/1980 | Curtis, Jr. |
| 5,171,628 | A | | 12/1992 | Arvedson et al. |
| 5,256,717 | A | | 10/1993 | Stauffer et al. |
| 5,331,033 | A | | 7/1994 | Stauffer et al. |
| 5,397,843 | A | | 3/1995 | Lakshmanan et al. |
| 5,478,891 | A | * | 12/1995 | Lakshmanan .......... C09J 123/10 524/528 |
| 5,723,546 | A | * | 3/1998 | Sustic ........................... 525/240 |
| 5,763,333 | A | | 6/1998 | Suzuki et al. |
| 6,045,900 | A | * | 4/2000 | Haffner et al. ............. 428/315.9 |
| 6,177,190 | B1 | * | 1/2001 | Gehlsen ................. C09J 123/02 428/355 EN |
| 6,329,468 | B1 | | 12/2001 | Wang |
| 6,653,385 | B2 | | 11/2003 | Wang et al. |
| 6,773,818 | B2 | | 8/2004 | Cretekos et al. |
| 6,833,404 | B2 | | 12/2004 | Quinn et al. |
| 6,846,876 | B1 | | 1/2005 | Quinn |
| 6,872,279 | B1 | | 3/2005 | Kolowrot et al. |
| 6,887,225 | B2 | * | 5/2005 | Strand ................. A61F 13/5611 604/385.01 |
| 7,015,155 | B2 | | 3/2006 | Zhou et al. |
| 7,067,585 | B2 | | 6/2006 | Wang et al. |
| 7,262,251 | B2 | | 8/2007 | Kanderski et al. |
| 7,270,889 | B2 | | 9/2007 | Campbell et al. |
| 7,348,376 | B2 | * | 3/2008 | Gelles ........................... 524/505 |
| 7,439,305 | B2 | * | 10/2008 | Hoffmann et al. ............ 525/191 |
| 7,517,579 | B2 | | 4/2009 | Campbell et al. |

(Continued)

FOREIGN PATENT DOCUMENTS

| JP | H04236288 A | 8/1992 |
|---|---|---|
| JP | 2000226561 A | 8/2000 |
| JP | 2009126991 A | 11/2009 |
| JP | 2009275218 A | 11/2009 |
| JP | 2013540843 A | 11/2013 |
| WO | 9709393 A1 | 3/1997 |
| WO | 2008063907 A1 | 5/2008 |

OTHER PUBLICATIONS

Eastman, "Bulk Handling and Storage of Molten EASTOFLEX™ Amorphous Polyolefins" (published Jul. 2013).*

(Continued)

*Primary Examiner* — Scott R Walshon

(74) *Attorney, Agent, or Firm* — Sun Hee Lehmann

(57) ABSTRACT

Adhesives, methods to bond substrates together with the adhesives, and articles of manufacture comprising the adhesives are described. It has been discovered that an adhesive with a polymer content greater than 70 weight percent can be formulated with a blend of (i) a metallocene catalyzed polypropylene polymer that has a density range of about 0.70 to about 0.91 g/cm$^3$ and a melt viscosity less than 50,000 cP at 190° C. and (ii) a Ziegler-Natta catalyzed amorphous polybutene and/or polypropylene copolymer. Such adhesives have high creep resistance making them particularly well suited for disposable personal care garments.

17 Claims, No Drawings

(56) References Cited

U.S. PATENT DOCUMENTS

| | | | |
|---|---|---|---|
| 7,786,032 B2 | 8/2010 | Zhou et al. | |
| 7,833,611 B2 | 11/2010 | Phan et al. | |
| 7,879,745 B2 | 2/2011 | Blenke et al. | |
| 8,076,407 B2* | 12/2011 | Ellis et al. | 524/515 |
| 8,623,480 B2* | 1/2014 | Davis | B32B 7/12 156/334 |
| 2004/0153046 A1* | 8/2004 | Ito | A61F 13/62 604/391 |
| 2005/0181207 A1 | 8/2005 | He et al. | |
| 2006/0089617 A1 | 4/2006 | Bunnelle | |
| 2007/0142801 A1 | 6/2007 | Zhou et al. | |
| 2009/0203847 A1* | 8/2009 | Ellis et al. | 525/221 |
| 2010/0305528 A1 | 12/2010 | Bunnelle et al. | |
| 2011/0021103 A1 | 1/2011 | Alper et al. | |
| 2011/0052929 A1 | 3/2011 | Nairn et al. | |
| 2012/0329353 A1* | 12/2012 | Davis | C09J 123/10 442/381 |

OTHER PUBLICATIONS

Eastotac Hydrocarbon Resins Brochure by the Eastman Company (Aug. 1992).
Specialty Polymers for Adhesives and Sealants by the Exxon Chemical Company (Oct. 1990).
Litz, R.J., Developments in Ethylene-Based Hot Melt Adhesives, Adhesives Age 17(8):35-38 (1974).
Clark, T., Bookbinding with Adhesives (3rd ed. McGraw-Hill, UK 1994), p. 1.
Alger, Mark S.M., Polymer Science Dictionary (Elsevier Applied Science, New York 1989), p. 115.
Lee, S.M., Dictionary of Composite Materials Technology (Technomic Publishing Company, Inc., 1989) p. 43.
Young, R.J. & Lovell, P.A., Introduction to Polymers (2nd ed., Chapman & Hall, New York 1991), pp. 10-11, 292.
Handbook of Adhesives (ed. Irving Skeist, Van Nostrand Reinhold Co. 1977), pp. 495-498.
Kraus et al., Tack and Viscoelasticity of Block Copolymer Based Adhesives, J. Adhesion 10:221-36 (1979).
Eastman Chemical Brochure titled "World of Eastman Chemicals" dated Jan. 1989, Publication No. P-160F.
Eastman AQ Branched Polyesters Brochure dated Sep. 1997, Publication No. WA-62B.
Eastman Chemical Sales Brochure dated Feb. 1993, Publication No. WA-21.
Exxon Chemical Sales Brochure dated Mar. 1994.
Eastman Chemical Eastotac Hydrocarbon Resins dated Nov. 1994, Publication WA-3C.
Exxon Chemical Escorez Tackifiers Brochure dated Apr. 1992.

* cited by examiner

ADHESIVES AND USE THEREOF

This application is a continuation of International Patent Application No. PCT/US2012/048131 filed Jul. 25, 2012, which claims priority to U.S. Provisional Patent Application No. 61/515,013 filed Aug. 4, 2011, the contents of both of which are incorporated herein by reference.

FIELD OF THE INVENTION

The present invention relates to high polymer content adhesive for use on nonwoven articles. The adhesive is useful in disposable absorbent articles such as diapers, feminine hygiene articles, adult incontinence articles, underpads, bed pads, industrial pads and the like.

BACKGROUND OF THE INVENTION

Generally, a disposable absorbent article, such as a diaper, has several adhesives because various parts of the article require different functionality: core adhesives add strength to the diaper pad when it is wet; construction adhesives bind the waterproof backsheet to the nonwoven absorbent pads; and elastic adhesives bind legs, waist and lateral panel sheets. While the aforementioned adhesives perform different functionality, all of them typically require significant amounts of tackifier and/or diluents to be useful as adhesives.

Olefin-based adhesives have typically been used as core and construction adhesives. While widely used, olefin-based adhesives require large amounts of tackifiers and plasticizers to be effective absorbent article adhesives. For example, sprayable ethylene and/or maleic acid modified ethylene α-olefin polymer based adhesives typically require greater than 30 wt % of tackifiers and/or diluents. Use of high levels of oil in adhesives can lead to oil migration out of substrates at elevated temperature.

Amorphous atactic poly-α-olefins (APAO) adhesives are widely used as construction adhesives for nonwovens. These adhesives are typically chosen as construction and/or core adhesive, and not selected as elastic adhesives.

A blend of atactic and isotactic polyethylene polymers (IPP) and a blend of atactic and sydiotactic polypropylene (SPP) have been used to balance the cohesive and adhesive strength of the adhesive. Even with the balanced properties of cohesive and adhesive strength, the above adhesives do not have the required performance characteristics of an elastic adhesive.

While recent polymer technology has introduced block olefin polymers which allows for better creep resistance, large quantities of low molecular weight plasticizers are required in the adhesives, and this negates the creep performance at elevated temperatures. The amount of the block olefin polymer in the adhesive is less than about 50 wt %, preferably less than 30 wt %, and most preferably less than about 20 wt %, based on the total weight of the adhesive. Adhesives made with polymers that have blocks of regular isotactic structure, interdispersed by segments of atactic structure, still require at least 30, and up to 70 wt % of a tackifier, based on the total weight of the adhesives.

Because of the insufficient elastic performance, many commercially available elastic adhesives are styrene block copolymers based. Adhesives made from such block copolymers are readily available and are described in the art. The hard block of styrenes anchor onto the substrate and hold its shape, allowing for elasticity. However, styrene-based adhesives also require large quantities of tackifier and/or diluents to balance the application temperature and viscosity.

While low crystalline (less than 10%) content adhesives based on butene poly-α-olefin are known, such adhesives are not suitable for elastic substrates due to its stiffness.

There continues to be a need in the art for cost-effective adhesives with desirable cohesion and creep resistance with low tackifiers and plasticizer content. The current invention addresses this need.

BRIEF SUMMARY OF THE INVENTION

The invention provides novel adhesives, methods of using the adhesives to bond substrates together, and articles of manufacture comprising the adhesives. It has been discovered that a high polymer content adhesive can be formulated with a blend of a metallocene catalyzed polymers, and an olefin amorphous polybutene copolymer. Such adhesives contain at least 70 wt % of the polymer blend.

In one embodiment, the adhesive of the present invention comprises (a) at least 70 wt % of a polymer blend, which comprises (i) a metallocene catalyzed polypropylene polymer that has a density range of about 0.70 to about 0.91 g/cm$^3$ and a melt viscosity less than 50,000 cP at 190° C., and (ii) an amorphous copolymer selected from the group consisting of polybutene copolymer, polypropylene copolymer and mixtures thereof; and (b) less than 30 wt %, but not 0 wt %, of a tackifier and/or diluent. The components of the adhesive add to 100 wt % of the adhesive. The adhesive has a viscosity below about 11,000 centipoise at 150° C. in accordance with ASTM D3236.

Yet in another embodiment, the metallocene catalyzed polypropylene polymer of the elastic adhesive is an isotactic polypropylene homopolymer or copolymer.

In another embodiment, the metallocene catalyzed polypropylene polymer of the adhesive is atactic polypropylene homopolymer or copolymer.

Another embodiment of the invention is directed to articles of manufacture comprising the adhesives described herein. Articles of manufacture encompassed by the invention include disposable personal care garments such as diapers, sanitary napkins, incontinent pads, bed pads, feminine pads, panty shields, meat pads, and the like.

Another embodiment of the invention is directed to a method of forming an article by (1) applying an adhesive onto a substrate at a temperature of about 140° C. to about 160° C. and (2) cooling the adhesive to room temperature, wherein the cooled adhesive has a creep resistance of less than about 40% after 300% strain is applied onto the cooled adhesive at 38° C. for about 4 hours. The adhesive comprises (a) at least 70 wt % of a polymer blend, which comprises (i) a metallocene catalyzed polypropylene polymer that has a density range of about 0.70 to about 0.91 g/cm$^3$ and (ii) an amorphous polybutylene and/or polypropylene copolymer; and (b) less than 30 wt % of a tackifier and/or diluent; and the adhesive has a viscosity below about 11,000 centipoise (cP) at 150° C.

DETAILED DESCRIPTION OF THE INVENTION

All documents cited herein are incorporated in their entireties by reference.

All weight percentages (wt %) are calculated from the total weight of the adhesive, and the total weight of the adhesive is 100 wt %.

The term "polymer" as used herein, refers to homopolymers or copolymers. The copolymers are any polymers that have at least two monomers.

The term "metallocene catalyzed polymer" as used herein, refers to metallocene catalyzed homopolymer or metallocene catalyzed copolymers.

The term "metallocene catalyzed propylene polymer" as used herein, refers to metallocene catalyzed propylene homopolymer or metallocene catalyzed propylene copolymers.

The adhesive of the present invention comprises at least 70 wt % of a polymer blend. The polymer blend is a mixture of (i) a metallocene catalyzed polypropylene polymer, and (ii) an amorphous polybutene and/or polypropylene copolymer.

Metallocene catalyzed polymers are polymerized by metallocene catalysts which impart narrow molecular weight and composition distributions and sterospecificity. Narrow molecular weight distribution refers to low polydispersity index (PDI) which is the weight average molecular weight (Mw) divided by the number average molecular weight (Mn). Preferable PDI range for the metallocene catalyzed polymers is less than 3.

In one embodiment, the preferred metallocene catalyzed polymer is a metallocene catalyzed polypropylene homopolymer or metallocene catalyzed polypropylene copolymer with a comonomer. In another embodiment, the comonomer of the metallocene catalyzed polypropylene copolymer is a $C_2$, $C_4$-$C_{10}$ α-olefin comonomer. Yet in another embodiment, the comonomer is an ethylene and/or butylene.

The density range of the metallocene catalyzed polypropylene polymer ranges from about 0.70 to about 0.91 g/cm$^3$.

In another embodiment, the metallocene catalyzed polypropylene polymer is low in molecular weight and low in its modulus. In one aspect, the molecular weight ranges from about 10,000 to about 200,000 Daltons, with a molecular distribution of about 1 to about 4.

The metallocene catalyzed polypropylene polymer has a range of melting temperature of about 38° C. to about 104° C., and its melt viscosity range of about 200 to 100,000,000 cP at 190° C.

It is preferable that the melt viscosity of the metallocene catalyzed polypropylene polymer at 190° C. ranges from about 500 to about 80,000 cP, more preferably up to about 50,000 cP. Exemplary metallocene catalyzed polypropylene polymers include L-MODU™ X400S, X600S and X901S from Idemitsu.

In another embodiment, the polymer has a melt flow rate greater than 50 g/10 min at 230° C. and 2.16 kg weight. Exemplary metallocene catalyzed polypropylene polymers include VISTAMAXX 2000 polymer series from Exxon-Mobil.

In another aspect, the modulus of the metallocene catalyzed polypropylene polymer ranges from about 20 to about 500 MPa at 80° C.

Yet in another embodiment, the metallocene catalyzed polypropylene polymer is isotactic, where the substituents are located on the same side of the polymer backbone. Isotactic polymers are usually semicrystalline and often form a helix configuration. Particularly preferred metallocene catalyzed polypropylene polymer has medium range isotacticity.

The amorphous homopolymers and copolymers are polymers produced by Ziegler-Natta catalysts. With Ziegler-Natta catalysts, the produced amorphous polymers have wider molecular weight ranges and composition distributions. The amorphous polymers produced with Ziegler-Natta catalysts are non-stereospecific, e.g., atactic in its morphology. The PDI of the amorphous polymers range from 3 to 10. Preferred amorphous polymers have PDI range of 5 to 6.

In one embodiment, the amorphous polymers are poly-α-olefin polymers that have a melt viscosity range greater than about 500 cP to about 10,000, more preferably 500 cP to 3,000 cP at 190° C. (determined in accordance with ASTM D3236).

The preferred amorphous poly-α-olefin polymer is amorphous polybutene and/or amorphous polypropylene copolymers. The comonomer of the polybutene is $C_2$-$C_3$ and $C_5$-$C_{10}$ α-olefin comonomer. The comonomer of the polybutene is $C_3$ α-olefin comonomer. The comonomer of the polypropylene is $C_2$ and $C_4$-$C_{10}$ α-olefin comonomer. In one aspect, the comonomer of the polypropylene is $C_2$ α-olefin comonomer. Exemplary amorphous poly-α-olefin copolymers include REXTAC E and RT polymer series from Rextac; VESTOPLAST polymer series from Evonik; and EASTOFLEX polymer series from Eastman, and the like.

In another embodiment, the ratio of the metallocene catalyzed polypropylene polymer to the amorphous polymer is in the range of 1:10 to about 1:1.

The adhesive further comprises a tackifier and/or a diluent. Desirable adhesive can be formulated with less than 30 wt %, less than 25 wt %, less than 23 wt % or less than 20 wt %, but greater than 0 wt % of a tackifier and/or diluent.

Exemplary tackifiers have a ring and ball softening point, typically measured in accordance with ASTM E28-58T, greater than 80° C. In another embodiment, the adhesive comprises a tackifier with a ring and ball softening point greater than 100° C.

Useful tackifying resins may include any compatible resin or mixtures, such as aliphatic petroleum hydrocarbon resins; and aromatic petroleum hydrocarbon resins and the hydrogenated derivatives thereof, having a softening point, as determined by ASTM method E28-58T, of greater than 80° C.; natural and modified rosins including, for example, as gum rosin, wood rosin, tall oil rosin, distilled rosin, hydrogenated rosin, dimerized rosin, resinates, and polymerized rosin; glycerol and pentaerythritol esters of natural and modified rosins, including, for example as the glycerol ester of pale, wood rosin, the glycerol ester of hydrogenated rosin, the glycerol ester of polymerized rosin, the pentaerythritol ester of hydrogenated rosin, and the phenolic-modified pentaerythritol ester of rosin; copolymers and terpolymers of natural terpenes, including, for example, styrene/terpene and alpha methyl styrene/terpene; polyterpene resins; and phenolic modified terpene resins and hydrogenated derivatives thereof including, for example, the resin product resulting from the condensation, in an acidic medium, of a bicyclic terpene and a phenol.

Examples of hydrogenated aliphatic tackifiers particularly suitable include ESCOREZ' 1000 series from Exxon Mobil Chemicals, ARKON P tackifiying resin series from Arakawa and REGALITE S1100 tackifying resin series from Eastman Chemical. Also included are the cyclic or acyclic $C_5$ resins and aromatic modified acyclic or cyclic resins, and examples include ESCOREZ® 2000 and 5000 series from Exxon Mobil. Example of a commercially available rosins and rosin derivatives that could be used to practice the invention includes SYLVALITE RE series available from Arizona Chemical. Examples of commercially available polyterpene resins include PICCOLYTE S, C, F, and A tackifying resin series from Pinova. Particularly preferred polyterpene is Piccolyte S115.

Preferred tackifiers are synthetic hydrocarbon resins. Included are aliphatic or cycloaliphatic hydrocarbons, aromatic hydrocarbons, aromatically modified aliphatic or cycloaliphatic hydrocarbons and mixtures thereof. Non-limiting examples include aliphatic olefin derived resins such as those available from Exxon under trade name and the ESCOREZ tackifying resin series. Eastotac series from Eastman are also useful in the invention. Preferred for this invention are Escorez 5400 from Exxon and Eastotac grades H100R and H130R from Eastman Chemical.

Non-limiting examples include aliphatic olefin derived resins such as those available from Exxon under trade name and the ESCOREZ® series. Eastotac series from Eastman are also useful in the invention.

Also useful are aromatic hydrocarbon resins that are natural and modified polyterpenes and cyclic and acyclic $C_9$ resins, available from Sartomer and Cray Valley under the trade name Norsolene and from Rutgers series of TK aromatic hydrocarbon resins.

Alpha methyl styrene such as KRISTALEX tackifying resin series from Eastman Chemicals, SYLVARES SA tackifying resin series with a ring and ball softening point greater than 80° C. from Arizona chemicals are also useful as tackifiers in the invention. Mixtures of two or more described tackifying resins may be required for some formulations.

Small quantities of alkyl phenolic tackifiers can be blended with additional tackifier agents detailed above to improve the high temperature performance of these adhesives. Alkyl phenolics added in less than 20 wt % of the total weight of the adhesive are compatible and in the proper combination increase high temperature adhesive performance. Alkyl phenolics are commercially available from Arakawa Chemical under the TAMANOL trade name and in several product lines from Schenectady International.

Exemplary diluents include plasticizers. Suitable plasticizers include oil, polybutenes, polyisobutylene, benzoates, adipic esters and the like. Particularly preferred plasticizers include polybutenes and polyisobutylenes, mineral oil, aliphatic oils, olefin oligomers and low molecular weight polymers, vegetable oil, animal oils, paraffinic oil, naphthenic oil, aromatic oil, long chain partial ether ester, alkyl monoesters, epoxidized oils, dialkyl diesters, aromatic diesters, alkyl ether monoester and mixtures thereof.

The adhesives of the present invention may desirably also contain at least one stabilizer and/or at least one antioxidant. These compounds are added to protect the adhesive from degradation caused by reaction with oxygen induced by such things as heat, light, or residual catalyst from the raw materials such as the tackifying resin.

Among the applicable stabilizers or antioxidants included herein are high molecular weight hindered phenols and multifunctional phenols such as sulfur and phosphorous-containing phenol. Hindered phenols are well known to those skilled in the art and may be characterized as phenolic compounds which also contain sterically bulky radicals in close proximity to the phenolic hydroxyl group thereof. In particular, tertiary butyl groups generally are substituted onto the benzene ring in at least one of the ortho positions relative to the phenolic hydroxyl group. The presence of these sterically bulky substituted radicals in the vicinity of the hydroxyl group serves to retard its stretching frequency, and correspondingly, its reactivity; this hindrance thus providing the phenolic compound with its stabilizing properties. Representative hindered phenols include; 1,3,5-trimethyl-2,4,6-tris-(3,5-di-tert-butyl-4-hydroxybenzyl)-benzene; pentaerythrityl tetrakis-3(3,5-d i-tert-butyl-4-hydroxyphenyl)-propionate; n-octadecyl-3(3,5-di-tert-butyl-4-hydroxyphenyl)-propionate; 4,4'-methylenebis(2,6-tert-butyl-phenol); 4,4'-thiobis(6-tert-butyl-o-cresol); 2,6-di-tertbutylphenol; 6-(4-hydroxyphenoxy)-2,4-bis(n-octyl-thio)-1,3,5 triazine; di-n-octylthio)ethyl 3,5-di-tert-butyl-4-hydroxy-benzoate; and sorbitol hexa[3-(3,5-d i-tert-butyl-4-hydroxy-phenyl)-propionate].

Such antioxidants are commercially available from Ciba Specialty Chemicals and include IRGANOX® 565, 1010, 1076 and 1726 which are hindered phenols. These are primary antioxidants which act as radical scavengers and may be used alone or in combination with other antioxidants such as phosphite antioxidants like IRGAFOS 168 antioxidant available from Ciba Specialty Chemicals. Phosphite catalysts are considered secondary catalysts and are not generally used alone. These are primarily used as peroxide decomposers. Other available catalysts are CYANOX® LTDP available from Cytec Industries and ETHANOX® 330 available from Albemarle Corp. Many such antioxidants are available either to be used alone or in combination with other such antioxidants. These compounds are added to the hot melts in small amounts, typically less than about 10 wt %, and have no effect on other physical properties. Other compounds that could be added that also do not affect physical properties are pigments which add color, or fluorescing agents, to mention only a couple. Additives like these are known to those skilled in the art.

The adhesives of the invention may optionally comprise additives, such as waxes, pigments, dyestuffs and fillers.

Waxes suitable for use in the adhesives include paraffin waxes, microcrystalline waxes, polyethylene waxes, polypropylene waxes, by-product polyethylene waxes, Fischer-Tropsch waxes, oxidized Fischer-Tropsch waxes and functionalized waxes such as hydroxy stearamide waxes and fatty amide waxes. High density low molecular weight polyethylene waxes, by-product polyethylene waxes and Fischer-Tropsch waxes are conventionally referred to in the art as synthetic high melting point waxes.

When used, the wax component will typically be present in amounts of up to about 10 wt %. Adhesives comprising a wax component will more typically comprise from about 0.5 to about 5 wt % of a wax. Preferred waxes have a melt temperature between 49° C. and 121° C., more preferably between 66° C. and 120° C., and most preferable between 82° C. and 115° C.

Depending on the contemplated end uses of the adhesives, other additives such as pigments, dyestuffs and fillers conventionally added to hot melt adhesives may be incorporated in minor amounts, i.e., up to about 10% by weight, into the formulations of the present invention.

While adhesives made from metallocene catalyzed polymers tend to have narrow PDI, good sprayability and high cohesive strength, they also have high viscosity, rigidity and require large amounts of tackifier and oil. On the other hand, adhesives made from Ziegler-Natta catalyzed amorphous olefins tend to have high polymer content and low viscosity, however, sprayability and cohesive strengths deteriorate. A mere combination of the two polymers exacerbates the disadvantages of each of the polymers. Such combination results in adhesive with low polymer content, high viscosity, high PDI and sometimes even incompatibility. Surprisingly, adhesives with minimal diluents and/or tackier and good cohesive forces can be realized with specific blends of metallocene catalyzed polymers and Ziegler-Natta catalyzed amorphous polymers. Namely, a combination of a metallocene catalyzed polypropylene polymer that has a density range of about 0.70 to about 0.91 g/cm³ and a melt viscosity range of about 1,000 to about 10,000 cP at 190° C. with a Ziegler-Natta catalyzed amorphous polybutene and/or polypropylene polymer results in a compatible polymer system that allows for minimal diluents and tackifier with good cohesive forces. The adhesive of the invention requires less than 30 wt %, less than 25 wt %, less than 23 wt % or less than 20 wt % of a tackifier and/or diluent to achieve acceptable creep resistance.

The adhesive compositions of the present invention are prepared by blending the components in a melt at a temperature about 170° C. to form a homogeneous blend. Various methods of blending are known in the art and any method that produces a homogeneous blend. The blend is then cooled and may be formed into pellets or blocks for storage or shipping. These pre-formed adhesives can then be reheated to apply onto substrates.

Hot melt application of adhesives are well known to one of skill in the art. The adhesives of the present invention may be applied to a desired substrate by any method known in the art, and include, without limitation roll coating, painting, dry-brushing, dip coating, spraying, strand-coating, slot-coating, swirl spraying, printing (e.g., ink jet printing), flexographic, extrusion, atomized spraying, gravure (pattern wheel transfer), electrostatic, vapor deposition, fiberization and/or screen printing. For coating applications, various patterns, such as continuous, intermittent, signature, and the like, can be applied to elastic substrates.

In another embodiment of the invention, a method for bonding a substrate to a similar or dissimilar substrate is provided. The method comprises applying to at least a first substrate a molten adhesive of the present invention, bringing a second substrate in contact with the adhesive applied to the first substrate, and allowing the composition to solidify, thereby the first and second substrates are bonded together, wherein the adhesive of the present invention preferably comprises (a) at least 70 wt % of a polymer blend which comprises (i) a metallocene catalyzed polypropylene polymer that has a density range of about 0.70 to about 0.91 g/cm$^3$ and (ii) an amorphous polybutylene copolymer; and (b) less than 30 wt % of a tackifier and/or diluent, wherein the ratio of the (i) metallocene catalyzed polypropylene polymer to the (ii) amorphous polybutylene copolymer is in the range of 1:10 to about 1:1, and the total weight of the adhesive is 100 wt %. The substrates may be alike or dissimilar. Multiple substrates can be joined together with the adhesive.

"Substrates" as used herein, comprises polymeric films such as, but not limited to: polyolefin; polyester; polyurethane; polyamide; polyacrylate; or combinations thereof, including random, block, or graft copolymers such as polyester-b-polyurethane block copolymers, polyether-b-polyurethane block copolymers, styrenic block copolymers, and/or polyether-b-polyamide block copolymers. Examples of elastic strand include LYCRA, a multifilament elastomeric thread sold by Invista, Inc., GLOSPAN, an elastic strand made by Globe Manufacturing Company and CONFI-FIT elastic strand, from Fulflex.

For those composites comprising adhesive, "creep-resistance" or "creep-resistance value" refers to the holding power of a particular adhesive. The creep resistance is a measure of the quality of the adhesive bond between the substrates.

The hot melt adhesives of the invention find use in, for example, the elastic portions of the personal care garments. Different from diaper reattachment tabs, elastic portions bind legs, waist and lateral panel sheets which require elasticity and resistance to shape deformation. Moreover, the hot melt adhesive of the invention may also be used as construction and/or core adhesives of the personal care garment.

Materials with excellent stretchability and elasticity are needed to manufacture a variety of disposal and durable articles such as, for example, incontinence pads, disposable diapers, training pants, clothing, undergarments, sports apparel, automotive trim, weather-stripping, gaskets, and furniture upholstery. Stretchability and elasticity are performance attributes that can, for example, function to effectuate a closely conforming fit to the body of a wearer or to the frame of an item. While numerous materials are known to exhibit excellent stress-strain properties and elasticity at room temperatures, it is often desirable for elastic materials to provide a conforming or secure fit during repeated use, extensions and retractions at elevated temperatures such as at body temperatures or in automobile interiors during summer months. The adhesives find particular use as elastic adhesive for use in non-woven applications such as baby diaper or adult incontinence items.

EXAMPLE

Components

L-MODU 400 PP is metallocene catalyzed polypropylene copolymer from Idemitsu with a melt viscosity of about 7,000 cps at 190° C. and modulus of 60 MPa.

Vistamaxx 6202 is a metallocene catalyzed polypropylene copolymer from Exxon with a Mass Melt Flow Rate (MFR) of 18 g/10 min at 230° C./2.16 kg.

VERSIFY 4300 polymer is a metallocene catalyzed polypropylene copolymer from Dow Chemical with a MFR of 25 g/10 min at 230° C./2.16 kg.

INFUSE 9807.15 polymer is a metallocene catalyzed ethylene-octene block copolymer available from DOW Chemicals with a MFR 15 g/10 min at 190° C./2.16 kg.

XUS 38608.00 is a metallocene catalyzed ethylene-octene random copolymer available from DOW Chemical with a MFR of 1200 at 190° C./2.16 kg.

REXTAC RT2830 polymer is an amorphous copolymer (propylene-butene) produced by Ziegler-Natta catalyst with a Brookfield viscosity of 3,000 cps at 190° C.

REXTAC RT2814 polymer is an amorphous copolymer (propylene-butene) produced by Ziegler-Natta catalyst with a Brookfield viscosity of 1,400 cps at 190° C.

REXTAC RT2315 polymer is an amorphous copolymer (ethylene-propylene) produced by Ziegler-Natta catalyst with a Brookfield viscosity of 1,500 cPs at 190° C.

ESCOREZ 5400 tackifying resin is a cycloaliphatic hydrocarbon resins available from Exxon Mobil with a softening point of 103° C.

EASTOTAC H130R tackifying resin is an aliphatic hydrocarbon resin available from Eastman Chemical with a softening point of 130° C.

EASTOTAC H-100r tackifying resin is an aliphatic hydrocarbon resin available from Eastman Chemical with a softening point of 100° C.

WINGTACK 98H tackifying resin is an aliphatic hydrocarbon resin available from Cray Valley with a softening point of 98° C.

INDOPOL H300 polybutene is a liquid polybutene available from INEOS oligomers with a molecular weight of 1300 Mn.

KRYSTOL Oil is a technical grade white mineral oil available from Petro Canada.

KAYDOL Oil is a technical grade white oil available from Sonneborn.

IRGANOX 1010/225 antioxidant is a hindered phenol antioxidant, available from Ciba Specialty Chemicals.

Rubber-based control A adhesive is DISPOMELT EL897B adhesive, a styrenic block copolymer based adhesive available from Henkel Corporation.

Rubber-based control B adhesive is DISPOMELT 898B adhesive, a styrenic block copolymer based adhesive available from Henkel Corporation.

Test Methods

Viscosity was measured at 302° F. (150° C.) using a standard Brookfield viscometer, spindle 27, ASTM D3236.

For an intermittent elastic coating: the length of a filament (e.g., spandex) adhered in the stretched condition between two nonwoven sheets or a nonwoven sheet and a polymeric film is measured and marked ("starting length"). Both ends of the spandex are cut outside of the adhesive bonding area (the intermittent area). The amount that the resulting free-end filament retracts is measured following a 4 hour period at 38° C. The percent creep is then calculated in the following manner:

$$\% \text{ creep} = \frac{\text{starting length} - \text{final length}}{\text{starting length}} \times 100\%$$

For example, if the initial distance between marks is 20 cm and the final distance between the marks is 15 cm, the percent creep is 25%. Preferably, five samples for each condition are tested and the results averaged for each elastic strand.

For a continuous elastic coating: The length of a filament (e.g., spandex) adhered in the stretched condition between two nonwoven sheets or a nonwoven sheet and a polymeric film is measured and marked ("starting length"). A sample length is taken outside of the marked area. The spandex filaments are then cut at the marked area. The amount that the filament retracts is measured following a 4 hour period at 38° C. The percent creep is then calculated in the following manner $$\% \text{ creep} = \frac{\text{starting length} - \text{final length}}{\text{starting length}} \times 100\%$$

Rubber based adhesives typically results in high creep resistance or acceptable creep resistance. Acceptable creep resistance of the adhesive is about 35% or less.

When testing creep performance by either spiral or strand application, the non-woven substrate used is 13.5 gsm spunbond, made by Avgol, the polypropylene film is 0.5 mil Pliant poly film, supplied by Pliant Corporation, and the spandex used is 620 Decitex (LYCRA®XA®) and the draft of the fiber was 4.0x.

When measuring creep performance for a bond made through strand coating, adhesive is applied at a temperature in the range of about 140° C. to about 160° C. on the nonwoven substrate and spandex with a strand coating pattern in a continuous or intermittent mode using a high speed laminator at 300 fpm and an open time of 0.1 sec and an ITW omega applicator. The adhesive add on level is 25-35 mg/m/strand with three elastic fibers.

When measuring creep for a bond made through spiral coating, adhesive is applied at a temperature in the range of about 140° C. to about 160° C. on the nonwoven substrate and spandex with an unwrapped spiral pattern in an intermittent mode using high speed laminator at 300 fpm with 0.1 sec open time and a Nordson 0.018" spiral applicator. The adhesive add-on level is 12 gsm with three elastic fibers being attached to the non-woven substrate.

To measure the peel strength, laminates were prepared by spraying the adhesive at 2.5 gsm through Signature nozzle head between 140° C.-160° C. onto a substrate and then applying a second substrate on the adhesive to form a bond. Typical substrates are non-woven fabric materials that typically have a basis weight in the range of about 10 to 25 gsm and flexible sheet-like film substrates such as polyolefin, e.g., polyethylene nonwovens or polypropylene nonwovens, polyurethane films, polyurethane foams, films or mouldings of cellulose derivatives, such as tissues, films or mouldings of polyacrylates or polymethacrylates, films or moulding of polyesters. The adhesive according to the invention may be used to bond alike or different substrates together.

Peel strength was measured by Sintech 1/D instron tester at 23° C. and 50% relative humidity with a two inch laminate sample. The laminate sample is separated at a rate of 12 inches/min at an angle of 180°. The peel result is expressed in W/in. The coating laminate was tested at least 72 hours after the bond was made.

Sample Preparation

Samples listed in Table 1-3 were prepared by using techniques known in the art. The components to each adhesive samples are listed in the Table. An exemplary procedure involved placing approximately half of the total tackifier in a jacketed mixing kettle, which is equipped with rotors, and raising the temperature to a range from about 100° C. to about 170° C. When the tackifier melted, stirring was initiated and the rest of the components were added until a homogeneous mass was obtained.

The viscosity of several samples were measured.

TABLE 1

Viscosity of Ziegler-Natta and Metallocene Catalyzed Olefin Blends

|  | Sample 1 | Comparative Sample A | Comparative Sample B | Comparative Sample C |
| --- | --- | --- | --- | --- |
| Ziegler-Natta catalyzed amorphous polymer | 60 wt % Rextac 2830 | 60 wt % Rextac 2830 | 60 wt % Rextac 2830 | 60 wt % Rextac 2830 |
| Metallocene catalyzed polymer | 20 wt % L-MODU 400S (melt viscosity is 7,000 cP at 190° C.) | 20 wt % VISTAMAXX 6202 polymer (MFR is 18 g/10 min at 230° C./2.16 kg) | 20 wt % INFUSE 9807.15 polymer (MFR is 18 g/10 min at 190° C./2.16 kg) | 20 wt % VERSIFY 4300 polymer (MFR is 25 g/10 min at 230° C./2.16 kg) |

TABLE 1-continued

Viscosity of Ziegler-Natta and Metallocene Catalyzed Olefin Blends

|  | Sample 1 | Comparative Sample A | Comparative Sample B | Comparative Sample C |
|---|---|---|---|---|
| Viscosity at 150° C. (cP) | 9,500 | 21,200 | 18,680 | 17,000 |

Only Sample 1 had viscosity lower than 11,000 cP at 150° C. Comparative Samples A-C had viscosities greater than 11,000 cP at 150° C., which is too high to be applied at standard application temperatures.

Adhesive samples were applied by continuous elastic coating application methods and their creep resistances were measured and reported in Table 2.

TABLE 2

Elastic Creep Resistance using Continuous Elastic Coating Application Method

|  | Rubber-based Control A | Comparative Sample A | Comparative Sample B |
|---|---|---|---|
| Metallocene catalyzed polypropylene |  | 0 | 0 |
| Ziegler-Natta catalyzed amorphous polymer |  | 70 wt % Rextac RT 2814 | 100 wt % Rextac RT 2830 |
| tackifier |  | 29.7 wt % Eastotac H130R |  |
| antioxidant |  | 0.3 wt % Irganox 1010 |  |
| Viscosity at 150° C. (cP) | 10500 | 3500 | 10000 |
| Creep (%), 35 mg/m/s | 15 | 68 | 54 |
| Creep (%), 25 mg/m/s | 22 | 68 | 56 |
| Creep (%), 12gsm spiral | 27 | 67 | 49 |

Rubber-based adhesives are typically used as elastic adhesive for they have acceptable creep values. Acceptable creep % for an adhesive is less than about 35%. Table 2 shows that amorphous polymer based adhesives have significantly higher creep values than a typical rubber-based elastic adhesive.

Adhesive samples were applied by intermittent elastic coating application methods and their creep resistances were measured and reported in Table 3.

TABLE 3

Elastic Creep Resistance using Intermittent Elastic Coating Application Method

|  | Sample 1 |
|---|---|
| Metallocene catalyzed polymer | 19.9 wt % L-MODU 400 |
| Ziegler-Natta catalyzed amorphous polymer | 59.9 wt % REXTAC RT2830 polymer |
| tackifier | 19.9 wt % ESCOREZ 5400 tackifying resin |
| antioxidant | 0.3 wt % IRGANOX 1010 antioxidant |
| Viscosity at 150° C. (cP) | 9,500 |
| Creep (%), 35 mg/m/s | 2 |
| Creep (%), 25 mg/m/s | 26 |
| Creep (%), 12gsm spiral | 32 |

The creep resistance for Sample 1 was similar to the Rubber-based adhesive.

Laminated articles were prepared, as described above, by applying the adhesive in a with a Signature pattern with a Universal Signature Continuous Spray Nozzle at an add-on level of 2.5 gsm. Peel adhesion tests were conducted on the laminated samples and their values are reported in Table 4.

TABLE 4

Peel Adhesion, Signature Pattern

|  | Rubber-based Control B | Comparative Sample C | Comparative Sample D | Sample 2 |
|---|---|---|---|---|
| Metallocene catalyzed polypropylene |  |  |  | 25 wt % L-MODU 400 |
| Metallocene catalyzed polyethylene |  | 13 wt % Infuse 9807.15 | 15 wt % XUS38608.00 |  |
| Ziegler-Natta catalyzed amorphous polymer |  | 7 wt % Rextac RT 2315 | 55 wt % RT 2814 | 40 wt % Rextac RT 2814 |
| tackifier |  | 60 wt % Wingtack 98 | 25 wt % Eastotac H-130R | 30 wt % Eastotac H-100R |
| Additive - oil |  | 20 wt % Kaydol Oil | 5 wt % Indopol H-300 | 5 wt % Krystol Oil |
| antioxidant |  | 0.5 wt % Irganox 1010 | 0.3 wt % Irganox 1010 | 0.3 wt % Irganox 1010 |
| Viscosity at 150° C. (cP) | 2700 | 2500 | 4800 | 3650 |
| Initial Peel Strength in gf/in | 220 | 230 | 110 | 482 |

The initial peel strength of the laminated article with Sample 2 was higher than the rubber based adhesive and comparative sample C. Sample C also had similar initial peel strength as the rubber based adhesive, but requires large quantities of tackifiers and diluents to achieve the sprayable viscosity. Sample D, while high in polymer content, the peel strength is low. Thus, a specific combination of the metallocene catalyzed polypropylene and Ziegler-Natta catalyzed amorphous polymer is necessary to achieve good peel strength and acceptable creep resistance.

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

We claim:

1. An adhesive comprising:
   a) at least 70 wt % of a polymer blend which consists of:
      i) a metallocene catalyzed polypropylene homopolymer that has a density range of about 0.70 to about 0.91 g/cm$^3$ and a melt viscosity less than 50,000 cP at 190° C.,
      ii) an atactic polypropylene-polybutene copolymer; and
      iii) optionally, a metallocene catalyzed-propylene copolymer with a $C_2$, $C_4$-$C_{10}$ α-olefin comonomer; and
   b) less than about 30 wt % of a tackifier and/or plasticizer;
   wherein adhesive has a viscosity below about 11,000 centipoise at 150° C. as measured in accordance with ASTM D3236;
   wherein the ratio of (i) the metallocene catalyzed polypropylene homopolymer to (ii) the atactic polypropylene-polybutene copolymer is in the range of from about 1:1 to about 1:10; and
   wherein the total weight adds to 100 wt %.

2. The adhesive of claim 1 wherein the adhesive comprises less than about 25 wt % of the tackifier and/or plasticizer.

3. The adhesive of claim 1 wherein the metallocene catalyzed polypropylene homopolymer is an isotatic polypropylene.

4. The adhesive of claim 1 wherein the metallocene catalyzed polypropylene homopolymer is an atactic polypropylene.

5. The adhesive of claim 1 wherein the viscosity of the atactic polypropylene-polybutene copolymer is in the range of from about 500 cP to about 3,000 cP at 190° C.

6. The adhesive of claim 1 wherein the tackifier is selected from the group consisting of natural and modified polyterpenes, cyclic or acyclic $C_5$ resins, cyclic or acyclic $C_9$ resins, aliphatic and aromatic petroleum hydrocarbon resins, and mixtures thereof.

7. The adhesive of claim 6 wherein the tackifier has a softening point greater than about 80° C.

8. The adhesive of claim 1 further comprising up to about 10 wt % wax.

9. The adhesive of claim 1 wherein the metallocene catalyzed polypropylene homopolymer has medium range isotacticity.

10. A disposable article comprising an adhesive, wherein the adhesive comprises:
    a) at least 70 wt % of a polymer blend which consists of:
       i) a metallocene catalyzed polypropylene homopolymer that has a density range of about 0.70 to about 0.91 g/cm$^3$ and a melt viscosity less than 50,000 cP at 190° C.,
       ii) an atactic polypropylene-polybutene copolymer having a non-stereospecific morphology; and
       iii) optionally, a metallocene catalyzed-propylene copolymer with a $C_2$, $C_4$-$C_{10}$ α-olefin comonomer; and
    b) less than about 30 wt % of a tackifier and/or plasticizer;
    wherein adhesive has a viscosity below about 11,000 centipoise at 150° C. as measured in accordance with ASTM D3236;
    wherein the ratio of (i) the metallocene catalyzed polypropylene homopolymer to (ii) the atactic polypropylene-polybutene copolymer is in the range of from about 1:1 to about 1:10; and
    wherein the total weight adds to 100 wt %.

11. The disposable article of claim 10 which is an elastic attachment.

12. The disposable article of claim 11 comprising a substrate wherein the substrate is a film formed from a material selected from the group consisting of rubber, olefin, and a mixture thereof.

13. A method of forming an article comprising:
    a) applying the adhesive of claim 1 onto a substrate at a temperature of about 140° C. to about 160° C.;
    b) cooling the adhesive to room temperature; and
    wherein the cooled adhesive has a creep performance of less than about 40% after 300% strain is applied onto the cooled adhesive at 38° C. for about 4 hours.

14. The method of claim 13 wherein the adhesive is applied by strand coating or spiral coating.

15. The method of claim 13 wherein the adhesive is applied with an add-on level of about 20 to about 100 mg/m/strand.

16. The method of claim 13 wherein the adhesive is applied with an add-on level of about 3 to about 30 mg/inch.

17. The method of claim 13 wherein the cooled adhesive has a creep performance of less than about 30% after 300% strain is applied onto the cooled adhesive at 38° C. for about 4 hours.

* * * * *

UNITED STATES PATENT AND TRADEMARK OFFICE
CERTIFICATE OF CORRECTION

PATENT NO. : 9,695,341 B2
APPLICATION NO. : 14/169353
DATED : July 4, 2017
INVENTOR(S) : Jennifer Thatcher, Yuhong Hu and Darshak Desai Page 1 of 1

It is certified that error appears in the above-identified patent and that said Letters Patent is hereby corrected as shown below:

In the Specification

Column 10, Line 38: Change "Win" to -- g/in --.

Signed and Sealed this
Twenty-second Day of May, 2018

Andrei Iancu
*Director of the United States Patent and Trademark Office*